United States Patent [19]

Duch et al.

[11] Patent Number: 4,512,992

[45] Date of Patent: * Apr. 23, 1985

[54] TREATMENT WITH DIALKOXY PYRIDOPYRIMIDINE COMPOUNDS

[75] Inventors: David S. Duch, Gary; Charles A. Nichol, Durham; Carl W. Sigel, Raleigh, all of N.C.

[73] Assignee: Burroughs Wellcome Co., N.C.

[*] Notice: The portion of the term of this patent subsequent to Feb. 8, 2000 has been disclaimed.

[21] Appl. No.: 231,977

[22] Filed: Feb. 6, 1981

Related U.S. Application Data

[63] Continuation of Ser. No. 159,241, Jun. 13, 1980, abandoned.

[51] Int. Cl.³ .............................................. A61K 31/505
[52] U.S. Cl. ...................................... 514/258; 514/863
[58] Field of Search .......................................... 424/251

[56] References Cited

U.S. PATENT DOCUMENTS 3,322,765  5/1967  Hitchings et al. ................. 424/251

FOREIGN PATENT DOCUMENTS 913710  12/1962  United Kingdom ................ 424/251
970583   9/1964  United Kingdom ................ 424/251
1084103  9/1967  United Kingdom ................ 424/251

*Primary Examiner*—Jerome D. Goldberg
*Attorney, Agent, or Firm*—Donald Brown

[57] ABSTRACT

This application is directed to treatment of psoriasis with a pyrido pyrimidine compound such as 2,4-diamino-6-(3,4-dimethoxybenzyl)-5-methylpyrido[2,3-d]pyrimidine.

8 Claims, No Drawings

TREATMENT WITH DIALKOXY PYRIDOPYRIMIDINE COMPOUNDS

This is a continuation of application Ser. No. 159241 filed June 13, 1980, now abandoned.

The present invention relates to 2,4-diaminopyrido(2,3-d)pyrimidines, to pharmaceutical formulations comprising such compounds and to their use in medicine.

U.K. Pat. No. 1 084 103 discloses 2,4-diaminopyrido(2,3-d)pyrimidines of the general formula (I) in which $R^1$ is an alkyl group and $R^2$ is an unsubstituted

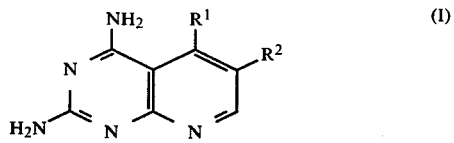

benzyl group or a benzyl group substituted by one or more halogen atoms, alkyl or alkoxy groups.

The compounds of formula (I) were described as having high in vitro and in vivo activity against bacteria or bacterial infections in experimental animals.

It has subsequently been found that the compounds of formula (I) specifically disclosed in U.K. Pat. No. 1 084 103 show some inhibitory activity against mammalian dihydrofolate reductase (DHFR), and the activity was sufficient to render them potentially useful in the treatment of conditions where inhibition of mammalian DHFR is desirable. It has further been found that many of these compounds are potent inhibitors of histamine N-methyltransferase (HMT), an enzyme involved in the metabolism of histamine. In this manner they often cause an undesirable accumulation of histamine in organs and tissues. The effects of histamine are well known and any possibility of a further utility for these compounds was substantially diminished by their strong inhibition of HMT.

Further investigation showed that a number of other compounds of formula (I) also possess DHFR inhibitory activity but that these, too, were also potent inhibitors of HMT. Others which had acceptably low levels of inhibition of HMT, were found to have insufficient activity as inhibitors of DHFR.

It has now been surprisingly found that 2,4-diamino-6-(3,4-dimethoxybenzyl)-5-methylpyrido[2,3-d]pyrimidine, which is within the scope of formula (I) but not specifically disclosed in U.K. 1 084 103, is not only a very potent inhibitor of mammalian DHFR, but also has acceptably low inhibitory activity against HMT. These compounds are represented by formula (II) below and are useful in the treatment of psoriasis.

The invention herein accordingly set forth the antipsoriasis properties of compounds of formula (II):

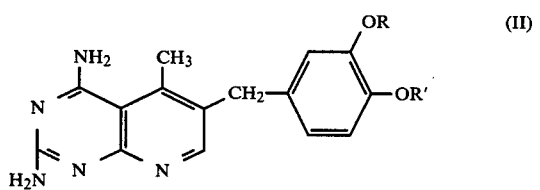

wherein R and R' are lower ($C_1$–$C_6$) alkyl, and pharmaceutically acceptable acid addition salts thereof. Preferably monobasic salts are provided. Preferably R and R' are methyl.

The compounds of formula (II) and their use in the treatment of bacterial infections caused by *Pasteurella boviseptica, Shigella dysenteriae,* and the genus Mycobacteria were discovered earlier by another whose rights are assignable to Burroughs Wellcome C.

The antipsoriasis activity of the compound of formula (II) resides in the free base and thus the nature of the acid participating in the acid addition salts is of minor importance. Such acid addition salts include, for example, those derived from hydrochloric acid, hydroiodic acid, sulphuric acid, phosphoric acid, acetic acid, p-toluenesulphonic acid, methanesulphonic acid, maleic acid, lactic acid, citric acid, tartaric acid, succinic acid, oxalic acid, p-chlorobenzenesulphonic acid, glucuronic acid, pantothenic acid isethionic acid and lactobionic acid.

The compound of formula (II) may be prepared by any method known to the art for the preparation of compounds of analogous structure.

In particular the compound of formula (II) may be prepared by the reductive cleavage of the corresponding 7-substituted compound of formula (III):

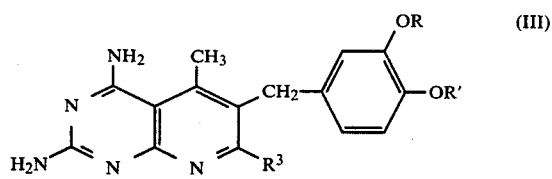

wherein R and R' are as defined above and $R^3$ is a leaving group capable of being removed by hydrogenolysis. Such groups include for example a mercapto or halogeno (e.g. chloro) group.

Where in the compound of formula (III) $R^3$ is SH the dethiation may for instance be conveniently effected by reaction with a reducing agent, for example Raney nickel or Raney cobalt or by catalytic hydrogenation utilizing hydrogen in the presence of a catalyst such as palladium on charcoal.

The compound of formula (III) wherein $R^3$ is a mercapto group may be prepared from the corresponding 7-chloro compound [(III), $R^3$=Cl] by reaction with a hydrosulfide as described in U.K. Pat. No. 913 710 or by treatment of the corresponding 7-hydroxy compound with phosphorous pentasulfide.

In the case where in the compound of formula (III) $R^3$ is a halogen atom, the compound of formula (II) may for instance be conveniently obtained by e.g. catalytic hydrogenation.

The compound of formula (II) may also be prepared by reacting 2,4,6-triaminopyrimidine (IV) with a compound of formula (V) wherein A is

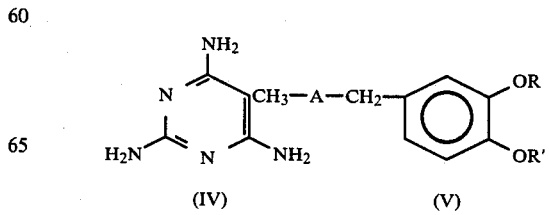

selected from

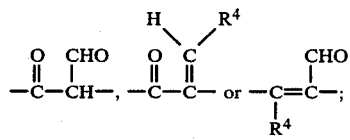

R and R' are as defined above; and $R^4$ is a leaving group such as for example a tertiary amino, alkoxy, alkylthio, halo, sulphonate or tosylate group.

The compound of formula (II) may additionally be prepared by the conversion to amino groups, by methods known in themselves in pyrimidine chemistry, of the hydroxy and/or mercapto group(s) in the compound of formula (VI):

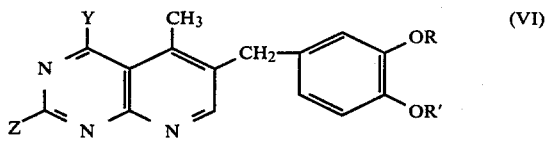

in which R and R' are as defined above and Y and Z are the same or different and are OH, SH, or $NH_2$ provided that at least one of Y and Z is OH or SH.

Compounds of formula (VI) may be prepared by methods known in the art for the preparation of such compounds. In addition, those in which Y is OH or $NH_2$ and Z is OH or SH may be obtained, for example, by reaction of urea, guanidine or thiourea with a suitable compound of formula (VII) in which R and R' are as defined above; $R^5$ is $-CO_2H$, $CO_2Alkyl$, $CONH_2$ or CN; and $R^6$ is

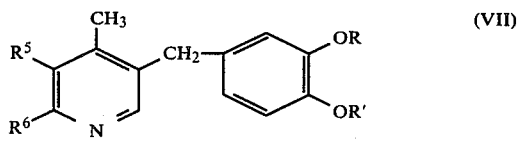

$NH_2$, Cl or Br.

While it is possible for the compound of formula (II) or an acid addition salt thereof (hereinafter referred to as the "active compounds") to be administered as the raw chemical it is preferably presented in the form of a pharmaceutical formulation.

The invention therefore further provides a pharmaceutical formulation comprising the active compound together with a pharmaceutically acceptable carrier therefore. The carrier must be "acceptable" in the sense of being compatible with the other ingredients of the formulation and not deleterious to the recipient thereof.

The invention additionally provides a method for the preparation of a pharmaceutical formulation comprising bringing into association an active compound and a pharmaceutically acceptable carrier therefor.

Topical application is particularly suitable when the active compounds are for use in the treatment of psoriasis skin diseases.

The term "topical" as applied herein relates to the use of the active ingredient incorporated in a suitable pharmaceutical carrier, and applied at the site of the disease for the exertion of local action.

Pharmaceutical formulations suitable for topical administration may be presented in anhydrous forms such as ointments, lotions, pastes, jellies, sprays, aerosols, and bath oils. The term ointment includes formulations (including creams) having oleaginous, absorption, water-soluble and emulsion type bases, for example petrolatum, lanolin, polyethyleneglycols and mixtures thereof.

Topical formulations may contain a concentration of the active ingredient of from about 0.05 to about 2% w/w, preferably about 0.1 to about 1% w/w, most preferably about 0.2 to about 0.5% w/w.

Other pharmaceutical formulations include those suitable for oral, rectal, and parenteral (including intramuscular and intravenous) administration although of these oral is preferred. The formulations may, where appropriate, be conveniently presented in discrete dosage units and may be prepared by any of the methods well known in the art of pharmacy. A convenient unit dose formulation contains the active compound in an amount of from about 50 mg to about 2 g, preferably about 100 mg to about 500 mg, most preferably about 200 mg, to be taken once or several times daily.

All methods for the preparation of such formulations include the step of bringing into association the active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active compound. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may be optionally scored. Capsules may be prepared by filling the active compound either alone or in admixture with one or more accessory ingredients, into the capsule cases and then sealing them in the usual manner. Cachets are analogous to capsules wherein the active ingredient together with any accessary ingredient(s) is sealed in a rice paper envelope.

Pharmaceutical formulations suitable for oral administration wherein the carrier is a liquid may be presented as a solution or a suspension in an aqueous liquid or a non-aqueous liquid, or as an oil-in-water or water-in-oil liquid emulsion.

Pharmaceutical formulations suitable for rectal administration wherein the carrier is a solid are most preferably presented as unit dose suppositories. Suitable carriers include cocoa butter and other material commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

As has been described above the compounds of the present invention are useful for the treatment of psoriasis. The invention thus further provides a method for the treatment of psoriasis in mammals including humans which comprises the administration of an effective, non-toxic amount of a compound of formula (II) or an acid addition salt thereof once or several times a day orally or applied topically.

The amount of compound of formula (II) required for therapeutic effect as an antipsoriasis agent will of course vary not only with the particular salt used but also with the route of administration. In general a suitable dose for the treatment of mammals (including humans) will lie in the range of from about 0.1 to about 100 mg per kilogram bodyweight (mg/kg) per day, preferably in the range of about 0.5 to about 20 mg/kg, most preferably in the range of about 1 to 10 mg/kg.

Toxic manifestations attributable to the active compound are typically those associated with folate depletion, such as bone marrow depression, megaloblastic changes, and gastrointestinal ulceration. Calcium leucovorin (calcium salt of 5-formyl-5,6,7,8-tetrahydrofolic acid) may be administered to effect reversal of these toxic manifestations or to prevent their occurrence. The administration of calcium leucovorin may be effected concurrently with treatment or at any stage thereof whenever toxic symptoms appear.

Thus, the haematological activity of the active compound can be prevented or reduced by the simultaneous administration of leucovorin. Consequently, tissue levels of the compound may be safely raised by increasing the dose of the compound together with a simultaneous administration of leucovorin.

EXAMPLE 1

2,4-Diamino-6-(3,4-dimethoxybenzyl)-5-methyl-pyrido[2,3-d]pyrimidine

A mixture of 3,4-dimethoxybenzaldehyde (100 g), ethyl acetoacetate (78 g) and anhydrous benzene (100 ml) was heated at reflux for 3 hours, during which time the theoretical amount of water was removed by azeotropic distillation. The solvent was then removed under reduced pressure and the residue recrystallised from ethyl acetate/pentane to give ethyl α-(3,4-dimethoxybenzylidene)acetoacetate (153 g), m.p. 72° C. (analytical sample from additional recrystallization (ethanol-pentane), m.p. 85°–86° C.).

Ethyl α-(3,4-dimethoxybenzylidene)acetoacetate (50 g) was catalytically reduced in a Parr low pressure apparatus in ethyl acetate (150 ml) in the presence of 5% palladium on charcoal catalyst (Pd/C)(3 g). The catalyst was removed by filtration; the solvent was removed under reduced pressure; and the residual oil was distilled to give ethyl α-(3,4-dimethoxybenzyl)-acetoacetate (40.5 g, b.p. 162°–164° C./0.4 mm Hg).

A mixture of ethyl α-(3,4-dimethoxybenzyl)acetoacetate (42 g) and 2,4,6-triaminopyrimidine (21 g) in diphenyl ether (120 ml) was heated at 190°–230° C. for 2 hours during which time the ethanol and water formed were azeotropically removed. The reaction was cooled, and methanol (250 ml) and ethanol (50 ml) were added. The resulting solid was collected by filtration and treated with boiling water (1) to give 2,4-diamino-5-methyl-6-(3,4-dimethoxybenzyl)-7-oxo-7,8-dihydropyrido[2,3-d]pyrimidine (26 g), m.p. 346°–348° C.

To a solution of dimethylformamide (17.5 g) in chloroform (75 ml) was added thionyl chloride (28.6 g) in chloroform (25 ml) at 0°–5° C. The reaction mixture was allowed to heat to 55°–60° for about 5 minutes and cooled to 0° C. To the reaction mixture was added over a 20 minute period at 0° C. 2,4-diamino-5-methyl-6-(3,4-dimethoxybenzyl)-7-oxo-7,8-dihydropyrido[2,3-d]-pyrimidine (8.2 g). Chloroform (50 ml) was added, and the mixture was heated at reflux for 2.5 hours and cooled. Ethanol in base (50 ml) was added. The resulting brown product was collected by filtration, treated with 2N sodium hydroxide and recrystallized from ethanol to give 7.6 g of crude product. Additional recrystallization from ethanol-water gave 2,4-diamino-5-methyl-6-(3,4-dimethoxybenzyl)-7-chloropyrido[2,3-d]pyrimidine (2 g), m.p. 224°–225° C. (dec.). This was added to ethanol (250 ml) containing potassium hydroxide (0.2 g), 5% palladium on charcoal catalyst (Pd/C, 0.1 g) was added and hydrogenation commenced. Reduction was complete after 4 hours in a Parr low-pressure apparatus at 35–40 psi and gave 2,4-diamino-6-(3,4-dimethoxybenzyl)-5-methylpyrido[2,3-d]pyrimidine (0.1 g), m.p. 265°–268° C. (dec.).

EXAMPLE 2

Inhibition of Mammalian Dihydrofolate Reductase (DHFR) by 2,4-P-amino-5-methyl-6-benzylpyrido(2,3-d)pyrimidines The inhibitory effect of the test compounds against DHFR partially purified from rat liver was determined. The results are given in Table 1 below. An $IC_{50}$ of $5 \times 10^{-8}$M or less is considered significant potency, an $IC_{50}$ of $1 \times 10^{-8}$M or less being particularly significant potency.

TABLE 1

| TEST COMPOUND $R^1$ | $R^2$ | $IC_{50} \times 10^{-8}$M |
|---|---|---|
| CH₃ | —CH₂—⟨phenyl⟩ | 4 |
| CH₃ | —CH₂—⟨phenyl⟩—CH₃ | 2.7 |
| CH₃ | —CH₂—⟨phenyl with Cl⟩ | 1.6 |
| CH₃ | —CH₂—⟨phenyl with CH₃O⟩ | 5.0 |

TABLE 1-continued

Structure: 2,4-diamino pyrido[2,3-d]pyrimidine with $R^1$ at 5-position and $R^2$ at 6-position.

| TEST COMPOUND R$^1$ | R$^2$ | IC$_{50}$ × 10$^{-8}$M |
|---|---|---|
| CH$_3$ | —CH$_2$—C$_6$H$_4$—OCH$_3$ | 5.3 |
| CH$_3$ | —CH$_2$—C$_6$H$_4$—C$_2$H$_5$ | 9 |
| H | —CH$_2$—C$_6$H$_5$ | 25 |
| CH$_3$ | —CH$_2$—C$_6$H$_3$(OCH$_3$)$_2$ (3,4-dimethoxybenzyl) | 0.78 |

EXAMPLE 3

Inhibition of Histamine N-Methyltransferase

The effect of the test compounds used in Example 2 against HMT was determined. The results are given in Table 2. An inhibition of less than 20% was considered acceptable.

TABLE 2

| TEST COMPOUND R$^1$ | R$^2$ | % Inhibition of HMT at 10$^{-5}$M |
|---|---|---|
| CH$_3$ | —CH$_2$—C$_6$H$_5$ | 51 |
| CH$_3$ | —CH$_2$—(2-Cl-C$_6$H$_4$) | 59 |
| CH$_3$ | —CH$_2$—(2-OCH$_3$-C$_6$H$_4$) | 18 |
| CH$_3$ | —CH$_2$—C$_6$H$_4$—OCH$_3$ (4-) | 20 |
| CH$_3$ | —CH$_2$—C$_6$H$_4$—C$_2$H$_5$ | 55 |
| H | —CH$_2$—C$_6$H$_5$ | 48 |
| CH$_3$ | —CH$_2$—C$_6$H$_3$(OCH$_3$)$_2$ (2,3- or 3,4-dimethoxy) | 19 |

EXAMPLE 4

Water Soluble Ointment

| | amount (g) |
|---|---|
| 2,4-Diamino-6-(3,4-dimethoxybenzyl)-5-methylprido[2,3-d]pyrimidine | 0.5 |
| Polyethylene glycol 300 | 20.0 |
| Polyethylene glycol 1500 | 79.5 |
| Total | 100.0 |

EXAMPLE 5

Skin Cream

| | amount (g) |
|---|---|
| 2,4-Diamino-6-(3,4-dimethoxybenzyl)-5-methylprido[2,3-d]pyrimidine | 0.5 |
| Glyceryl monostearate | 20.0 |
| Methylparaben | 0.3 |
| Petrolatum, light liquid | 4.0 |
| Propylene glycol | 5.0 |
| Span 60 | 2.0 |
| Tween 61 | 4.0 |
| Water | 64.2 |
| Total | 100.0 |

EXAMPLE 6

Injectable

| | amount |
|---|---|
| 2,4-Diamino-6-(3,4-dimethoxybenzyl)-5-methylprido[2,3-d]pyrimidine | qs to 5 mg/ml |
| Propylene glycol | 40 ml |
| Ethanol | 11 ml |
| Water | 49 ml |

EXAMPLE 7

Injectable

|  | amount |
| --- | --- |
| 2,4-Diamine-6-(3,4-dimethoxybenzyl)-5-methylpyrido[2,3-d]pyrimidine | qs to 5 mg/ml |
| Propylene glycol | 40 ml |
| 5% Dextrose solution | 60 ml |

We claim:

1. A method of treating psoriasis in a mammal suffering from psoriasis comprising the administration of a non-toxic, effective antipsoriasis amount of a compound of formula (II):

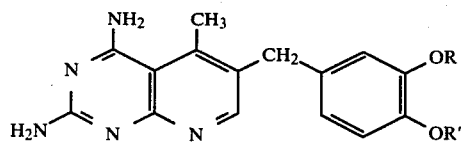

(II)

wherein R and R' are lower ($C_1$–$C_6$) alkyl, or pharmaceutically acceptable acid addition salt thereof to said mammal.

2. A method according to claim 1 in which said compound is 2,4-diamino-6-(3,4-dimethoxybenzyl)-5-methylpyrido[2,3-d]pyrimidine.

3. The method of claim 1 or 2 in which the compound or salt is administered in a pharmaceutically acceptable carrier.

4. The method of claim 1 or 2 in which the compound or salt is administered as a part of a topical formulation.

5. The method of claim 1 or 2 in which the compound or salt is administered as a part of a topical formulation in which the compound or salt is at a concentration of 0.05 to 2% w/w.

6. The method of claim 1 or 2 in which the compound or salt is administered as part of an oral preparation or parenteral preparation.

7. The method of claim 1 or 2 in which the compound or salt is administered in a pharmaceutically acceptable carrier in a form suitable for topical, parenteral or oral administration.

8. The method of claim 7 in which the amount of the compound or salt is 50 mg to 1 gram.

* * * * *